United States Patent [19]

Ben-Sasson

[11] Patent Number: 4,780,307

[45] Date of Patent: Oct. 25, 1988

[54] ALUMINUM HYDROXIDE

[75] Inventor: Shmuel Ben-Sasson, Jerusalem, Israel

[73] Assignee: Rafa Laboratories Ltd., Israel

[21] Appl. No.: 787,315

[22] Filed: Oct. 15, 1985

[30] Foreign Application Priority Data

Oct. 23, 1984 [IL] Israel .......................................... 73921

[51] Int. Cl.$^4$ ....................... C01B 31/24; A61K 33/10
[52] U.S. Cl. ..................................... 423/626; 423/629; 424/157
[58] Field of Search ................. 423/629, 626; 424/157

[56] References Cited

U.S. PATENT DOCUMENTS

| 2,137,638 | 11/1938 | Sondern et al. | 424/157 |
| 2,657,115 | 10/1953 | Ashley | 423/629 |
| 2,888,323 | 5/1959 | Teichner | 423/629 |
| 2,919,973 | 1/1960 | Stillwell et al. | 423/626 |
| 3,395,221 | 7/1968 | Snyder et al. | 423/629 |
| 3,773,918 | 11/1973 | Beekman | 423/629 |
| 3,798,160 | 3/1974 | Huffman | 423/629 |
| 4,059,681 | 11/1977 | Hem et al. | 424/157 |
| 4,105,579 | 8/1978 | Glasscock | 423/629 |
| 4,181,718 | 1/1980 | Mason et al. | 424/157 |
| 4,500,444 | 2/1985 | Beekman | 423/629 |

FOREIGN PATENT DOCUMENTS

| 484097 | 4/1938 | United Kingdom | 424/157 |
| 2123804 | 2/1984 | United Kingdom | 423/629 |

Primary Examiner—John Doll
Assistant Examiner—Wayne A. Langel
Attorney, Agent, or Firm—Steinberg & Raskin

[57] ABSTRACT

The present invention relates to the aluminum hydroxide having a specific surface area of at least 350 m$^2$, preferably at least 400 m$^2$, per g. and to a process for its preparation. The aluminum hydroxide should be capable of absorbing at least 1 g of fat per g. of material. The aluminum hydroxide is preferably part of a pharmaceutical preparation.

15 Claims, No Drawings

ALUMINUM HYDROXIDE

The present invention relates to an aluminium hydroxide having specific properties.

BACKGROUND OF THE INVENTION

Aluminium hydroxide is a known compound. Said known aluminum hydroxide has so far been utilized for medication as an antacid drug, often in combination with other antacid drugs. From the literature, e.g. White et al., J. Pharm. Sci. 64, 468 (1976); Kerkhof, J. Pharm. Sci. 66, 1533 (1977), it seems that the effect of said drug results apparently from the activity of aluminium carbonate admixed therewith.

From the literature it is known that said commercially available aluminium hydroxide has no dietary effect, i.e. it does not absorb foodstuffs and other nutritional factors. Thus, for example, the following statements can be found in the literature:
1. "Relatively large doses of aluminium hydroxide cream did not alter the nitrogen or fat content of the feces of three normal dogs on a standard diet." Beazell et al., Am. J. Digest. Dist. 5, 164–165 (1938).
2. The results show that the ingestion of aluminium hydroxide was without appreciable effect upon the utilization of fat and carbohydrate." "Administration of aluminum hydroxide to a normal subject did not interfere with the utilization of carbohydrate, fats or proteins of the diet." Grondahl et al., Am. J. Digest, Dis. 12, 197-199 (1945).
3. "There appears to be no significant effect of alumina gel upon the tolerance curves of amino acids, ascorbic acid, glucose and neutral fats. Certainly in the case of neutral fats the results are unequivocal." Hoffman et al., Gastroenterology 6, 50-61 (1946).
4. "Absorption of foodstuffs and nutritional factors is not sufficiently depressed to be important and the composition of the feces is unaffected." The Pharmacological Basis of Therapeutics, Goodman and Gilman, 3rd. Ed., The Macmillan Company, N.Y. 1965, pp. 995-997.

SUMMARY OF THE INVENTION

It has now surprisingly been found that there exists a specific aluminium hydroxide which does not show appreciable antacid activity. However, surprisingly, it adsorbs dietary lipids in a high efficiency and increases their excretion.

The present invention thus consists in an aluminium hydroxide having a specific surface area of at least 350 $m^2$ per g material. (hereinafter "the aluminium hydroxide").

The specific surface area in connection with the present invention is the surface area measured by the method of Eltantawy et al., J. Soil. Sci. 24, 232-238 (1973).

The aluminum hydroxide according to the present invention is capable of adsorbing at least 1 g of fat per g of the material.

The aluminium hydroxide according to the present invention has the following properties:
a. a relatively large surface area;
b. strong adsorption of dietary lipids;
c. high capacity of fat adsorption;
d. after oral administration causes an increase in the excretion of dietary lipids at the expense of the body intake; and
e. negligible antacid activity.

It is readily understood that the larger the specific surface area and the higher the fat adsorption capacity the better the properties of the aluminium hydroxide according to the present invention. Thus, the specific surface area is advantageously at least 400 $m^2/g$ and the absorption capacity at least 1.5 g of fat/g of the aluminium hydroxide.

The aluminium hydroxide according to the present invention may be administered as such, in the form of an aqueous suspension, in the form of a gel, etc.

The oral administration of the preparation comprising the aluminium hydroxide according to the present invention causes a decrease of the actual caloric value of a concomitantly ingested food.

The present invention consists also in a process for the preparation of the aluminium hydroxide which comprises the neutralization of an acidic or basic solution of a suitable aluminium salt with a suitable base or an acid, respectively, with subsequent heating after the neutralization reaction has been terminated.

The heating is advantageously performed at boiling temperature for at least 1 hour after the neutralization reaction has been terminated. Sometimes the heating operation will be performed after filtration and washing of the neutralization reaction mixture.

The process is preferably performed in diluted solutions.

The aluminium hydroxide is obtained by the above reaction either as a precipitate or as a gel and may be utilized as such.

It has been found that the stability of the aluminium hydroxide obtained by said process may be increased by drying it under mild conditions, e.g. between 20°–40° C. The dried compound is then re-suspended.

As suitable salts for the above reaction may be considered $AlCl_3$, $AlKSO_4$, $Al_2(SO_4)_3$, $NaAlO_2$; as acid HCl, $H_2SO_4$, acetic acid, propionic acid, butyric acid and valeric acid or a mixture thereof; and as base NaOH or KOH. However, it is readily understood that the present invention is not restricted to the use of the above salts, acids and bases.

DESCRIPTION OF THE PREFERRED EMBODIMENTS

The present invention will now be illustrated with reference to the following Examples without being limited by them.

EXAMPLE 1

Two L of distilled water in which 100 ml of n-butyric acid and 32 ml of n-valeric acid were dissolved, were neutralized in the cold by the gradual addition of an aqueous solution of 1N NaOH which contained 0.5N $NaAlO_2$. The resulting aluminium hydroxide suspension was then boiled for 2 hours and an aqueous solution of 1N NaOH was added for neutralization as the pH dropped during heating. The precipitate obtained was filtered off and washed thoroughly with distilled water. The washed precipitate was resuspended in distilled water to a volume of 800 ml and then let to dry at 37° C. Suspensions of about 5% aluminium hydroxide in distilled water. (Hereinafter refered to as "the 5% aluminium hydroxide) were prepared from the ground powder.

EXAMPLE 2

Two L of 0.5N acetic acid in distilled water were neutralized in the cold by a gradual addition of an aqueous solution of 1N NaOH which contained 0.5N NaAlO$_2$. The resulting aluminium hydroxide suspension was then boiled for 2 hours and an aqueous solution of 1N NaOH was added gradually for neutralization as the pH dropped during heating. The precipitate was filtered off and washed thoroughly with distilled water. The washed precipitate was resuspended in distilled water to a final volume of 800 ml, boiled for 1½ hours and then let to dry in 37° C. Suspensions of the 5% of aluminium hydroxide in distilled water were prepared from the ground powder.

EXAMPLE 3

10 g of pure aluminium metal were dissolved in 1 L of an aqueous solution of 1N NaOH and then neutralized with an aqueous solution of 1N HCl at room temperature. The resulting aluminium hydroxide suspension was then boiled for 1 hour. The precipitate was then filtered off and washed with distilled water. The washed precipitate was then resuspended in distilled water to a final volume of 600 ml, yielding a suspension of the 5% aluminium hydroxide.

EXAMPLE 4

One L of 5% AlCl$_3$.6H$_2$O in distilled water was neutralized with an aqueous solution of 2.5% NaOH at room temperature and then boiled for 1 hour. The resulting aluminum hydroxide precipitate was filtered off and washed with distilled water. The washed precipitate was then resuspended with distilled water to a final volume of 300 ml., yielding a suspension of the 5% aluminium hydroxide.

EXAMPLE 5

Measurement of specific surface area

The specific surface area of aluminium hydroxide preparations was determined by a gravimetric method, based on the retention of ethylene glycol monoethyl ether(EGME), as described in Eltantawy I. M. and Arnold P. W. (J. Soil Sci. 24, 232-238(1973)). The samples were first dried at 37° C., then ground and dried to constant weight over P$_2$O$_5$. 250 mg of aluminium hydroxide powder were wetted with 1 ml of EGME in weighing cup and processed according to the conditions of method (c) as described by Eltantawy and Arnold in the above paper. The specific surface area was calculated using the theoretical value of $3.71 \times 10^{-4}$ g of EGME for a complete unimolecular layer coverage of 1 m$^2$.

The results obtained are summarized in Table I.

TABLE I

| Aluminium hydroxide preparation | Specific surface area (m$^2$/g) |
| --- | --- |
| The aluminium hydroxide #1 | 735 |
| The aluminium hydroxide #2 | 611 |
| The aluminium hydroxide #3 | 413 |
| The aluminium hydroxide #4 | 538 |
| Alumina C$_\gamma$(Aged)* | 224 |
| Amphojel** | 85 |

*Alumina C$_\gamma$(Aged) is an aluminium hydroxide preparation manufactured by Sigma Chemical Co. (St. Louis, Mo. U.S.A.) and described by the producer as "An exceptionally active gel with high adsorptive capacity".
**Amphojel is a suspension of aluminium hydroxide gel manufactured for Wyeth Labs Inc. (Philadelphia Pa. USA) by Ayerst Labs Inc. (New York, NY USA). It is used as an antacid.

EXAMPLE 6

Demonstration of Antacid Capacity

1. Aluminium assay 5 g of the uniform suspension or gel prepared as described in any one of Examples 1 to 4 were dissolved in 7 ml of conc. HCl (ca. 32%) by warming on a water bath, and diluted to 100 ml in a volumetric flask. 10 ml of this solution were pipetted into a 250 ml beaker, 30 ml of a 0.025M disodium edetate solution were then added and the mixture was then neutralized with a 2M sodium hydroxide solution to a methyl red end point and 75 ml of water were then added. After warming on a water bath for 30 minutes and cooling to room temperature, 3 g of hexamine were added and the excess disodium edetate was back titrated with a ca. 0.025M lead (II) nitrate solution using xylenol orange as indicator. The aluminium content expressed as % Al(OH)$_3$ was calculated by the formula:

$$P = (0.025 \times 30 - M_{Pb} \times V_{Pb}) \times (78/W),$$

where
M$_{Pb}$ = the molarity of the lead (II) nitrate solution;
V$_{Pb}$ = the volume of the lead (II) nitrate solution consumed in the nitration, in ml;
W = the exact weight in g of the substance tested; and
P = the % Al(OH)$_3$ in the preparation.

2. Neutralizing capacity 50 ml of 0.1M hydrochloric acid solution were added to an aliquot of about 1 g of the uniform suspension or gel prepared as described in any of Examples 1 to 4 and the resulting mixture was shaken continuously at 37° C. for 1 hour. The excess acid was back tritrated with 0.1M sodium hydroxide solution and the end point was determined either visually by the colour change of bromophenol-blue indicator or potentiometrically at pH 3.5.

The acid neutralizing capacity, expressed in terms of milliequivalents of acid consumed per 1 g of a 5% preparation, was calculated by the following formula:

$$(M_{HCl} \times 50 - M_{NaOH} \times V_{NaOH}) \times 1/G \times 5/P,$$

where

M$_{HCl}$ = the molarity of the hydrochloric acid solution;
M$_{NaOH}$ = the molarity of the sodium hydroxide solution;
G = the exact weight in g of the tested substance;
V$_{NaOH}$ = the volume of the sodium hydroxide solution consumed in the titration, in ml; and
P = % Al(OH)$_3$ in the preparation obtained from the aluminium assay.

The results are summarized in Table II.

TABLE II

| Aluminium hydroxide preparation | Acid neutralizing capacity |
| --- | --- |
| The aluminium hydroxide #1 | 0.34 |
| The aluminium hydroxide #2 | 0.27 |
| The aluminium hydroxide #3 | 0.19 |
| The aluminium hydroxide #4 | 0.19 |
| Alumag | 3.6 |

The aluminium hydroxide is that according to the present invention. Alumag is a preparation of Zori Israel as described in Medic, 12, No. 4, July-August, 1983, p. 1.

EXAMPLE 7

Measurement of fat-adsorption capacity in vitro

The in vitro capacity of fat adsorption was determined using a radiolabelled triglyceride(TG). Glycerol tri[1-$C^{14}$]oleate, purchased from Amersham (Buckinghamshire, U.K.), was dissolved in pure olive oil to a final activity of about $10^7$dpm/ml olive oil. A stable emission of 1% TG was obtained by an intensive sonication of a mixture which contained 0.3 g of the radiolabelled olive oil and 29.7 ml of a solution of 4% oxbile extract in a 0.1M Tris-HCl buffer, pH 7.5. 1 ml of this emulsion was mixed with 1 ml of an aqueous suspension which contained various concentrations of the tested aluminium hydroxide preparation. After 5 min. incubation in room temperature, 8 ml. of distilled water were added and the mixture was let to stay at room temperature for 30 minutes with frequent mixing. The entire mixture was then filtered through a Whatman No. 41 filter paper and 0.5 ml of the filtrate was transferred to a counting vial. 10 ml of a toluene scintillation solution, containing 20% triton×100, were added to each vial. The amount of adsorbed TG was calculated by the relative radioactivity of the filtrate as compared to that of the control system (containing no aluminium hydroxide). The capacity is defined as twice the amount of grams of TG adsorbed by 1 gram of aluminium hydroxide at 50% yield of fat adsorption.

The point of 50% yield of fat adsorption was derived from the empirical isotherm proposed by Freundlich (W. J. Moore, Physical Chemistry 4th Ed., Longmans Green and Co. London, 1962, pp. 749-751).

The results obtained are summarized in Table III:

TABLE III

| Aluminium hydroxide preparation | TG adsorption capacity (grs TG/g Al(OH)$_3$ |
| --- | --- |
| The Aluminium hydroxide #1 | 2.7 |
| The Aluminium hydroxide #2 | 3.2 |
| The Aluminium hydroxide #3 | 2.1 |
| The Aluminium hydroxide #4 | 1.9 |
| Alumina C$_\gamma$(Aged) | 0.8 |
| Amphogel | 0.05 |

EXAMPLE 8

Demonstration of lipid adsorption in vitro 1 ml of a preparation of 5% aluminium hydroxide as described in Example 3 or 1 ml of a 5% suspension of a commercial (BDH) dry Al(OH)$_3$ in distilled water was mixed each with 1 ml of a solution of 2% ox bile extract (Sigma) in 50 mM of Tris buffer, pH 7.5, which contains a labeled lipid. The adsorption of the following lipids in each of the above preparations was tested:

$H^3$ Triloein (Amersham, 98% radiopure), $H^3$ cholesterol (at least 96% radiopure); and $H^3$ cholesteryl-lynoleyl-ether (97% radiopure).

The activity of the labeled compounds was adjusted to about $10^5$ dpm (disintegrations per minute) per system. Each assay was run in duplicate.

After incubation for 1 hour at room temperature, with occasional mixing, each tube was centrifuged (1000 g) for 20 minutes and 1 ml of the supernatant liquid was transferred to a counting vial. 10 ml of toluene sintillation solution containing 20% Triton X 100 were added to each vial.

The adsorption of the lipids was calculated according to the following equation:

%adsorption = [1-(dpm in the experiment/dpm in the control)]

The control system contains 1 ml of Tris buffer instead of the aluminium hydroxide preparation. The results obtained are given in Table IV.

TABLE IV

| adsorbant | % adsorption of radiolabeled lipids | | |
| --- | --- | --- | --- |
| | Triolein | Cholesterol | Cholesteryl-linoleyl-ether |
| The 5% aluminium hydroxide | 95% | 99.3% | 99.8% |
| 5% com. Al(OH)$_3$ | 0% | 0% | 46% |
| Control | 0% | 0% | 0% |

EXAMPLE 9

Demonstration of inhibition of intestinal lipids absorption in vivo

The following materials and methods were used in this Example:

Animals

Three months old Balb/c male mice each weighing about 25 g were used for all experiments. The mice were raised in the animal facility of the Hubert H. Humphrey Centre of the Medical School of the Hebrew University, Jerusalem. The mice were kept in temperature controlled rooms (about 24° C.) and fed the commercial laboratory chow diet.

Radiochemicals

Glycerol tri[1-$C^{14}$]oleate (97% radiopure by TLC) obtained from Amersham (Buckinghamshire, U.K.), $H^3$ trioleyl glyceryl ether, tritiated at C-2 of the glycerol carbon chain (at least 98% radiopure by TLC) prepared by the method described by J. Lab. Radiopharm. 20, 269 (1983).

Test meal

After the evaporation of the organic solvent, each radiochemical was dissolved in olive oil and admixed therewith. The average dose per mouse was 0.05 ml of test meal containing about $10^5$ dpm of the tritiated compound.

In the triolein ester:trioleyl ether mixture the $C_{14}$:$H^3$ ratio was about 1.5-2.

0.05 ml of olive oil-vehicle test meal was introduced by a gastic tube (intramedic polyethylene tubing PE90 or PE50, Clay Adams Inc., New York) connected to a 1 ml syringe through a Teflon catheter. In order to avoid bowel perforation the leading edge of the tube was wrapped with a short segment of a Silastic tube (Dow Corning Corp., Midland, Mich.). The administered amount was calculated precisely by syringe weighing.

Fecal collection

The method of anal cups described by Ryer et al., Lab. Anim. Sci. 21, 942 (1971) for rats was adapted for use in mice. Light, flexible cellulose nitrate tubes (ultracentrifuge tubes, Beckman, Palo Alto) of ⅜" dia.×2.5" height were found to be most suitable for this experiment. A rose shaped opening of about 0.5 cm diameter was drilled 1.5-2cm below the upper part of the tube. The tail was slipped through this hole and the tube was fitted to the mice body, leaving the penis outside. The tail was then taped to the tube. Each tube was weighed before and after the fecal collection and the harvest was transferred to a 50 ml glass tube for lipid extraction.

Experimental design

After an overnight fast, each mouse received a mixture of radioactive adsorbable lipid alongside with the nonadsorbable labeled analog in a total volume of 0.05 ml of olive oil, as described above. The feeding was performed by stomach intubation under slight ether anesthesia. For studying the effect of the various aluminium hydroxide preparations 0.25 ml of a 5% suspension of the preparation according to the present invention (four batches) in saline was introduced by a gastric tube 30 minutes prior to the introduction of the test meal. Another dose of 0.25 ml of the preparation was administered immediately after the test meal had been administered. In a similar manner the effect of an Alumag preparation was assayed.

The anal cup was then inserted and the animals were kept in separated cages, supplied with the regular diet, ad libidum. The fecal collection was terminated after 24 hours. The entire content of the removed cups was analysed.

Lipid extraction

An aqueous solution of 10% sodium dodecyl sulfate (SDS) was added to the feces in a ratio of 1.5 ml/1 g. (Usually a standard volume of 3 ml of SDC 10% was added to a 24 hour fecal collection). In order to achieve better dispersion, the preparations together with the detergent were incubated overnight at 37° C. and were admixed from time to time. The procedure of Bligh and Dyer (Can. J. Biochem. Physiol. 37, 911 (1959) for lipid extraction was applied to the fecal suspension (which usually was homogeneous). Assumingly the regular daily collection of mouse feces plus 3 ml of SDS 10% contains about 4 ml of water. (Slight variations of the water content should not interfere with the extraction procedure). Samples in duplicate, of 1 ml each, were taken from the separated chloroform phase. After complete evaporation of the solvent, 10 ml of toluene scintillation solution, which contained 20% of Triton×100 were added to the vials.

Calculation of adsorption

The percentage of lipid adsorption was calculated according to the isotope ratio method:

% lipid absorbed=1-(absorbable to nonabsorbable isotope ratio in the fecal collection/absorbalble to nonabsorbable isotope ratio in the test meal)]×100.

The results obtained are summarized in Table V.

TABLE V

| Oral administration | % Triglycerides excreted* |
|---|---|
| Saline (Control) | 2.8% + 0.8 (19) |
| The aluminium hydroxide #1 | 51% ± 6.4 (8) |
| The aluminium hydroxide #2 | 49% ± 7.9 (6) |
| The aluminium hydroxide #3 | 33% ± 6.1 (18) |
| The aluminium hydroxide #4 | 22% ± 9.1 (6) |
| Alumag | 3.9% ± 1.1 (9) |

*mean ± S.E.M. (standard error of the mean) as determined by the isotope ratio method;
(n) number of mice in each group
% excreted = 100 − % absorbed

EXAMPLE 10

Demonstration of body weight reduction by chronic administration of the aluminium hydroxide Albino, Israeli male mice, weighing around 30 g, were selected from the experiment. Three equal groups. of 10 mice each, were fed daily for 6 hours on a regular chaw diet. Prior to the beginning of the meal, the animals received by way of a gastric tube either 0.5 ml of saline (=group 1), or 0.5 ml of 6% suspension of the bile acids sequesting agent cholestyramine (=group 2), or 0.5 ml of 6% suspension of the aluminium hydroxide, preparation #2 (=group 3). The individual body weight was measured daily and the experiment lasted for a period of 75 days. The relative change in body weight in each group was compared to that of the control group (group 1).

While almost no difference in the pattern of body weight changes was observed between group 1 and group 2, the animals which received the aluminium hydroxide preparation (group 3) showed a significant reduction in their relative body weight:

After two weeks from the beginning of the experiment, their body weight was 7% lower than that of the controls and after 8 weeks the decrease reached was about 10%. It should be stressed that there was a slight increase (about 10%) in the food consumption by the animals of group 3, as compared to groups 1 and 2.

The average daily dietary intake under these experimental conditions was equivalent to about 300 calories per kg body weight.

I claim:

1. A process for preparation of an aluminium hydroxide for fat and lipid absorption upon administration, said aluminum hydroxide having a specific surface area of at least 400 $m^2/g$ and having a high degree of adsorption of dietary lipids and fats while having negligible antacid activity, comprising the steps of
   neutralizing an acidic or basic solution of an aluminum salt with a base or an acid, and
   after the neutralization reaction has been terminated, subsequently heating the thus-neutralized solution by boiling.

2. A process according to claim 1 being performed in a dilution solution.

3. A process according to claim 1, comprising the additional steps of
   drying the aluminum hydroxide compound obtained from the subsequent heating at 20°–40° C., and
   then resuspending the thus-dried aluminium hydroxide compound.

4. A process according to claim 3, wherein the drying operation is performed at about 37° C.

5. A process according to claim 1, wherin the aluminum salt is selected from $AlCl_3$, $AlKSO_4$, $Al_2(SO_4)_3$ and $NaAlO_2$.

6. A process according to claim 1, wherein the acid is selected from the group consisting of HCl, $H_2SO_4$, acetic acid, propionic acid, butyric and valeric acid or mixtures thereof.

7. A process according to claim 1, wherein the base is selected from NaOH and KOH.

8. The process of claim 1, comprising the additional steps of filtering and washing the neutralized reaction mixture before said heating step.

9. The process of claim 1, wherein the acid is a monocarboxylic acid.

10. The process of claim 9, wherein the monocarboxylic acid is acetic, n-butyric, or n-valeric acid.

11. The process of claim 1, wherein said neutralizing step is carried out in an aqueous medium.

12. The process of claim 1, additionally comprising heating the acidic or basic solution during the neutralizing thereof.

13. The process of claim 1, wherein the solution is neutralized with the acid.

14. The process of claim 1, wherein the solution is neutralized with the base.

15. A process according to claim 1, wherein the step of heating is performed for at least one hour, after the neutralization reaction has been terminated.

* * * * *